United States Patent [19]

Kasztreiner et al.

[11] Patent Number: 4,826,845

[45] Date of Patent: May 2, 1989

[54] 3(2H)-PYRIDAZINONES AND PHARMACEUTICAL COMPOSITIONS THEREOF

[75] Inventors: Endre Kasztreiner; György Rablócsky; Nándor Makk; László Jaszlits; Péter Mátyus; György Cseh; Ildikó Pribusz née Rapp; Klára Czakó; Eszter Diesler; Istv,e,acu/a/ n Elekes; László Kaufer; Mária Kuhár née Kürthy; Judit Kincsessy; Judit Kosáry; Gyöngyi Nagy née Csókás, all of Budapest, Hungary

[73] Assignee: Richter Gedeon Vegyeszeti Gyar T.R., Budapest, Hungary

[21] Appl. No.: 924,445

[22] Filed: Oct. 29, 1986

[30] Foreign Application Priority Data

Oct. 30, 1985 [HU] Hungary .............................. 4155/85

[51] Int. Cl.$^4$ .................. C07D 237/14; C07D 405/06; A61K 31/50; A61K 31/535

[52] U.S. Cl. .................................... 514/253; 544/114; 544/238; 544/239; 544/241; 514/247; 514/233.8; 514/236.5

[58] Field of Search ................... 544/241, 239, 238, 3, 544/55, 58.6, 111, 114; 514/247, 252, 253

[56] References Cited

U.S. PATENT DOCUMENTS

| | | | |
|---|---|---|---|
| 3,658,814 | 4/1972 | Houlihan | 544/239 |
| 4,298,609 | 11/1981 | Lesher et al. | 514/252 |
| 4,304,777 | 12/1981 | Lesher et al. | 514/252 |
| 4,521,416 | 6/1985 | Sircar et al. | 514/252 |
| 4,636,504 | 1/1987 | Kossy et al. | 514/252 |
| 4,666,902 | 5/1987 | Zoller et al. | 514/212 |

FOREIGN PATENT DOCUMENTS

| | | | |
|---|---|---|---|
| 42676 | 1/1982 | Japan | 544/239 |
| 146571 | 9/1983 | Japan . | |

Primary Examiner—Mark L. Berch
Attorney, Agent, or Firm—Keil & Weinkauf

[57] ABSTRACT

The invention relates to novel 3(2H)-pyridazinone-derivatives of the general formula (I), pharmaceutical compositions containing them and process for their preparation. In the general formula (I)

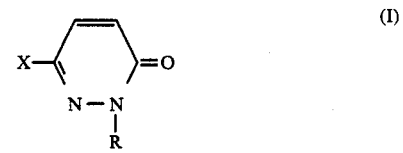

stands for an ethyl or propyl group substituted by a terminal halogen atom or a hydroxyl or $NR^1R^2$ group, wherein $R^1$ represents hydrogen atom or an unsubstituted or optionally substituted benzyl group;

$R^2$ represents hydrogen atom or an unsubstituted or optionally substituted benzo[1,4]dioxan-2-yl-methyl or -ethyl group or a $(CH_2)_n$—$R^3$ group, wherein n is 2 or 3; and $R^3$ stands for an unsubstituted or optionally substituted phenoxy or phenylthio group; and X stands for a hydrogen or halogen atom or an unsubstituted or optionally substituted, saturated or unsaturated 5- or 6-membered heterocyclic group containing a nitrogen atom and optionally an additional heteroatom, e.g. an oxygen, sulfur or nitrogen atom, with the proviso that R is different from an ethyl or propyl group substituted terminally by a hydroxyl group or halogen atom when X represents a hydrogen or chlorine atom.

The compounds of general formula (I) selectively inhibit the adrenergic alpha$_1$ receptors, have a calcium-antagonistic effect and exert blood pressure lowering action.

9 Claims, No Drawings

3(2H)-PYRIDAZINONES AND PHARMACEUTICAL COMPOSITIONS THEREOF

This invention relates to novel 3(2H)-pyridazinone derivatives. More particularly, the invention relates to new 3(2H)-pyridazinone derivatives of the general formula (I)

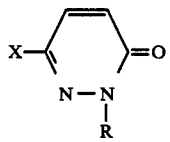

ps wherein
R stands for an ethyl or propyl group substituted by a terminal halogen atom or a hydroxyl or $NR^1R^2$ group, wherein
$R^1$ represents hydrogen atom or an unsubstituted or optionally substituted benzyl group;
$R^2$ represents hydrogen atom or an unsubstituted or optionally substituted benzo[1,4]dioxan-2-yl-methyl or -ethyl group of a $(CH_2)_n$—$R^3$ group, wherein
n is 2 or 3; and
$R^3$ stands for an unsubstituted or optionally substituted phenoxy or phenylthio group; and
X stands for a hydrogen or halogen atom or an unsubstituted or optionally substituted, saturated or unsaturated 5- or 6-membered heterocyclic group containing a nitrogen atom and optionally an additional heteroatom, e.g. an oxygen, sulfur or nitrogen atom,
with the proviso that R is different from an ethyl or propyl group substituted terminally by a hydroxyl group or halogen atom when X represents a hydrogen or chlorine atom, and the racemic and optically active variants thereof as well as the acid addition salts of these compounds.

Further on, the invention relates to the novel compounds of the general formula (IV)

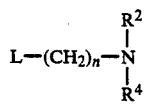

wherein
L stands for a chlorine, bromine or iodine atom or a lower alkanesulfonyloxy or unsubstituted or optionally substituted benzenesulfonyloxy group,
$R^2$ is as defined above, and
$R^4$ has the same meaning as $R^1$ defined above; and n is 3,
and the acid addition salts of these compounds, which are key substances for the preparation of compounds of the general formula (I).

The compounds of the general formula (I) of the invention show valuable pharmacodynamic activities: they selectively inhibit the adrenergic alpha$_1$ receptors, have a calcium-antagonistic effect and exert an outstanding blood pressure lowering action.

In a preferred group of the compounds of general formula (I) X stands for a hydrogen or chlorine atom and R stands for a propyl group terminally substituted by an $NR^1R^2$ group, wherein $R^1$ is a hydrogen atom and $R^2$ is as defined above.

In a particularly preferred group of the substances of the general formula (I) X means a hydrogen or halogen atom and R stands for a propyl group terminally substituted by an $NR^1R^2$ group, wherein $R^1$ represents a hydrogen atom and $R^2$ stands for a phenoxyethyl or benzo[1,4]dioxan-2-yl-methyl group.

Some 3(2H)-pyridazinones the structure of which is different from that of the compounds of the invention and which contain at the nitrogen atom in position 2 of the 3(2H)-pyridazinone nucleus various groups such as alkanecarboxylic acid groups [see, e.g. J. Am. Chem. Soc. 74, 3222 (1952); 78, 407 (1956)] or simple aminoalkyl groups (Bull. Soc. Chim. Fr. 1961, 606; 1962, 1117) are known in the literature. These compounds were prepared to achieve an antiinflammatory and analgetic effect but no therapeutic success was realized with them. No data were published on the circulatory (cardiovascular) action of these substances.

The compounds, wherein X represents a chlorine atom and R means an ethyl or propyl group terminally substituted by a hydroxyl group or a halogen atom, are also known in the literature [Monatsh. für Chem. 99, 15 (1968)].

It should be noted, however, that no adrenergic alpha$_1$ receptor-blocking or calcium-antagonistic effects of the known 3(2H)-pyridazinones have up to now been mentioned in the literature.

It is known that diseases related to the blood circulation, e.g. myocardial infarction and hypertension, are among the most frequent causes of death. The number of hypertensive patients continuously becomes higher.

Several types of blood pressure lowering agents are available to the physician which are characterized by the following examples.

The adrenergic beta-receptor-blocking agents such as metoprolol [chemically 1-[4-(2-methoxyethyl)phenoxy]-3-isopropylamino-2-propanol hydrogen tartrate] are mainly useful for treating the mild or moderately high hypertension. It has been shown in the last years that the blood lipid level is increased by their use what is, however, undesired in any case as it contributes to the process of the atherosclerosis.

The adrenergic alpha$_2$-agonists such as clonidine [chemically 2-(2,6-dichlorophenyl)-amino-2-imidazoline hydrochloride] are very effective antihypertensive drugs and also useful to treat the severely high hypertension. A drawback of this type of antihypertensive agents appears in a significant sedative side-effect as a consequence of their action on the central nervous system. This is disadvantageous for the work performance, particularly for the mental work.

Hydralazine (chemically 1-hydrazinophthalazine hydrochloride) is a characteristic representative of the antihypertensive agents based on the peripheral vasodilating action; their use is limited, however, by several harmful side-effects such as tachycardia (increase in the heart rate) as a reflectory consequence of the vasodilation.

Among the blood pressure lowering drugs, based on blocking the adrenergic alpha$_1$-receptor, prazosine [chemically 1-(4-amino-6,7-dimethoxy-2-quinazolinyl)-4-(2-furylcarbonyl)-piperazine hydrochloride] has gained the widest use.

In the recent years, a considerable attention was paid to the clinical utilization of the antihypertensive action of calcium-antagonists such as nifedipine [chemically 2,6-dimethyl-4-(2-nitrophenyl)-1,4-dihydropyridine-3,5-dicarboxylic acid dimethyl ester].

In spite of the results achieved, a continuing demand exists for novel blood pressure lowering agents free of side-effects, particularly for agents, the antihypertensive action of which is a resultant of several action components reinforcing another.

Now it has surprisingly been found in the course of our investigation that the novel 3(2H)-pyridazinone derivatives of the general formula (I) according to the invention, wherein R and X are the same as defined above, are capable to satisfy the demands of an antihypertensive effect "composed of several action components".

According to another aspect of the invention, there is provided a process for the preparation of the general formula (I) and the acid addition salts thereof, which comprises (a) condensing a compound of the general formula (II).

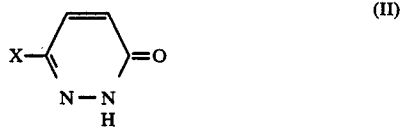

wherein X is the same as defined above, or a salt thereof with a compound of the general formula (IV) wherein L represents a leaving group, $R^2$ is the same as defined above and $R^4$ is the same as $R^1$ defined above, except hydrogen atom, or strands for a protective group and n is 2 or 3, to obtain compounds of the general formula (I), wherein X is the same as defined above and R stands for an ethyl or propyl group terminally substituted by an $NR^1R^2$ group, wherein $R^1$ and $R^2$ are the same as defined above, or (b) reacting a compound of the general formula (III),

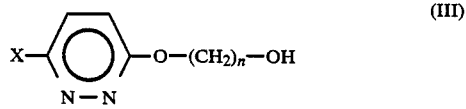

wherein X and n are the same as defined above, with a methanesulfonyl halide in the presence of a base and decomposing the reaction mixture with water, to obtain compounds of the general formula (I), wherein X is the same as defined above and R stands for an ethyl or propyl group terminally substituted by a halogen atom, or (c) reacting a compound of the general formula (I), wherein X is the same as defined above and R stands for an ethyl or propyl group terminally substituted by a halogen atom or by a lower alkanesulfonyloxy or unsubstituted or optionally substituted benzenesulfonyloxy group, with an amine of the general formula $HNR^1R^2$, wherein $R^1$ and $R^2$ are the same as defined above, or with a derivative thereof containing a protective group, to obtain compounds of the general formula (I), wherein X is the same as defined above and R stands for an ethyl or propyl group terminally substituted by an $NR^1R^2$ group, wherein $R^1$ and $R^2$ are the same as defined above, or (d) dehalogenating a compound of the general formula (I), wherein R is the same as defined above and X means a halogen atom, to obtain compounds of the general formula (I), wherein R is the same as defined above and X stands for a hydrogen atom, and, if desired, removing the protective group from a product obtained optionally containing a protective group by any of the processes (a) to (d) and/or, if desired, converting a base of the general formula (I) obtained by any of the above processes to an acid addition salt thereof in a known manner and/or, if desired, converting an acid addition salt thereof into an other acid addition salt thereof and/or, if desired, liberating the free base from the salts of the compounds of the general formula (I).

According to the definition accepted in the literature (see, e.g.: T. A. Geissman: Principles of Organic Chemistry, ed. 3; editor W. H. Freeman, London 1968) such groups are meant by the "leaving group" L which are relatively easy to displace by a nucleophilic agent. Such groups are e.g. the halogen atoms, particularly chlorine, bromine and iodine atoms as well as the lower alkanesulfonyloxy and the unsubstituted or optionally substituted benzenesulfonyloxy groups.

On carrying out the process of the invention, particularly preferred L groups are the chlorine and bromine atom as well as the methanesulfonyloxy and 4-toluenesulfonyloxy groups.

A preferred embodiment of process (a) of the invention comprises condensing an alkali metal salt, suitably the sodium or potassium salt, of a compound of the general formula (II) with a compound of the general formula (IV), wherein L preferably means chlorine atom, in the presence of an organic solvent or diluent. It is suitable to carry out the reaction in such a way that an alkali metal salt of the compound of the general formula (II) is previously prepared e.g. by treating it with a solution of sodium methoxide or potassium hydroxide in methanol, and removing the solvent, whereupon the thus-obtained alkali metal salt is condensed with a base of the general formula (IV) in the presence of an organic solvent or diluent. Aprotic solvents such as toluene or benzene may be used as solvents or diluents. It is suitable to use an organic quaternary ammonium salt as catalyst in the reaction.

The reaction is carried out at a temperature between 30° C. and 150° C., suitably at the boiling temperature of the solvent, e.g. benzene- or toluene-containing reaction mixture. On preparing compounds of the general formula (I), wherein the means of $R^1$ in $NR^1R^2$ is hydrogen atom, it may be suitable to use a compound of the formula (IV) wherein $R^4$ stands for e.g. a benzyl group which may be removed, when desired, by reduction, e.g. by catalytic hydrogenation.

According to a preferred embodiment of process b of the invention, a compound of the general formula (III), wherein X and n are the same as defined above, is reacted with methanesulfonyl chloride in an aprotic polar solvent, in the presence of an organic tertiary base such as triethylamine at a temperature between 0° C. and 10° C., whereafter the reaction mixture is left to stand at room temperature and then decomposed with ice-water. Dimethylformamide can suitably be used as polar aprotic solvent.

A preferred embodiment of process (c) of the invention comprises reacting a compound of the general formula (I) wherein R stands for an ethyl or propyl group terminally substituted by a halogen atom or an unsubstituted or optionally substituted benzenesulfonyloxy group, with an amine of the general formula NHR$^1$R$^2$ containing, if desired, a protective group, optionally in the presence of an acid binding agent and an organic solvent or diluent. Suitably, an anhydrous alkali metal carbonate, e.g. potassium carbonate is used, though an excess of the amine component may also be used for the same purpose. It is preferable to use dimethylformamide as solvent or diluent. This reaction is carried out at a temperature from 50° C. to 150° C.

According to an advantageous embodiment of process (d) of the invention, a compound of the general formula (I) containing a halogen atom, preferably a chlorine atom, in the position 6 of the 3(2H)-pyridazinone nucleus is catalytically hydrogenated e.g. in the presence of a palladium-on-carbon catalyst in an appropriate solvent. A lower aliphatic alkanol, e.g. methanol or ethanol, can preferably be used as solvent. Suitably, this reduction is accomplished by adding a basic acid-binding agent such as ammonia or an organic tertiary amine, e.g. triethylamine or an inorganic basic substance, e.g. potassium carbonate. The catalytic hydrogenation is accomplished under atmospheric pressure and at room temperature though higher pressures may also be employed, if desired.

The reaction mixture obtained as a result of the above-described processes may be worked up in a known manner e.g. by filtering off an inorganic salt or a catalyst optionally present, evaporating the filtrate under reduced pressure, mixing the residue with water and, when necessary, after alkalization of the reaction mixture, separating the thus-obtained product by filtration or extraction. If desired, the thus-obtained product can be purified by recrystallization or distillation. When the product is basic in character, it can be purified as it is, or converted to an acid addition salt, which in turn may be purified, if desired, by recrystallization.

It is obvious to a person skilled in the art that, when necessary, the compounds used in the processes (a) to (d) should be provided with protective groups in order to avoid any side-reaction. Such protective groups are well known. On preparing the compounds of the invention, the benzyl group can preferably be used which can conveniently be removed by hydrogenolysis, e.g. by catalyst hydrogenation after carrying out the aimed reaction.

The bases of the general formula (I) may be converted to an acid addition salt, suitably to a pharmaceutically acceptable acid addition salt thereof in a known manner, e.g. by dissolving the base in an appropriate organic solvent and adding portionwise the appropriate acid or a solution of this acid in a suitable solvent. The thus-obtained salt can be separated by filtration or by removing the solvent under reduced pressure and, if desired, purified in a known way, e.g. by recrystallization. A non-toxic inorganic acid such as hydrochloric or hydrobromic, sulfuric or phosphoric acid, or a non-toxic organic acid such as acetic, tartaric, maleic or fumaric acid can preferably be used as an acid component. When the acid component is inorganic, then a lower alkanol, e.g. ethanol or isopropanol or eventually acetone can suitably be used as solvent; when the acid component is organic, then a lower alkanol, e.g. ethanol or isopropanol, or a low-boiling aliphatic ketone, e.g. acetone or butanone, or an ether, preferably diethyl or diisopropyl ether, can conveniently be used as solvent.

Some of the compounds of the general formula (II) are known (see, e.g.: J. N. Mason: The Pyridazinones in: Heterocyclic Compounds, Vol. 28, Editor R. N. Castle, John Wiley and Sons, New York, pp. 65–69, 1973).

The compounds of the general formula (II) which are unknown in the literature can be prepared analogously to the processes used for the preparation of known substances.

A part of the compounds of the general formula (III) required in the process (b) of the invention (see, e.g.: J. N. Mason as cited above, p. 177; as well as Austrian patent specification No. 204,560) is known in the literature.

The preparation of the compound of the formula (III), wherein X stands for chlorine atom and n is 3, is described in Example 1. Other compounds of the general formula (III) are known or can be prepared analogously to the processes reported in the literature or to the process described in Example 1.

The amines of the general formula HNR$^1$R$^2$ are commonly known in the literature.

A part of the compounds of the general formula (IV) required to the embodiment of process (a) of the invention, is described [German patent specification No. 1,118,218].

The compounds of the general formula (IV), wherein n is 3 and R$^4$ is different from hydrogen atom, are new and also involved in the scope of the invention.

According to the invention, the compounds of the general formula (IV) are prepared by reacting a compound of the general formula (V),

$$HO-(CH_2)_3-\underset{R^4}{\overset{R^2}{N}} \qquad (V)$$

wherein R$^2$ and R$^4$ are as defined above, (a) with a halogenating agent to obtain compounds of the general formula (IV), wherein L stands for a chlorine, bromine or iodine atom, or (b) with a lower alkanesulfonyl chloride or an unsubstituted or optionally substituted benzenesulfonyl chloride to obtain compounds of the general formula (IV), wherein L represents a lower alkanesulfonyloxy or an unsubstituted or optionally substituted benzenesulfonyloxy group.

According to the invention, the compounds of the general formula (IV) are preferably prepared by treating an appropriate compound of the general formula (V) with a halogenating agent in an inert organic solvent. Thionyl chloride can conveniently be used as halogenating agent. An aromatic hydrocarbon such as benzene or particularly a chlorinated hydrocarbon, e.g. dichloromethane, can be used as solvent. The reaction is accomplished at a temperature between 0° C. and the boiling point of the reaction mixture.

Some of the compounds of the general formula (V) are known in the literature [see, e.g. the German patent specification No. 1,118,218]. The preparation of a compound of the formula (V) wherein R$^4$ represents benzyl group and R$^2$ stands for benzo[1,4]dioxan-2-yl-methyl group, is described in Example 12, step B). Other compounds of the general formula (V) can be prepared analogously to the methods reported in the literature or by using or similarly to the process described in Example 12, step B).

The blood pressure lowering action and other pharmacodynamic effects of the compounds of the general formula (I) were determined by using the methods described hereinafter.

Measurement of the hypotensive effect on anaesthetized cats

A tube was introduced into the trachea of cats anaesthetized by the intraperitoneal (i.p.) administration of 35 mg/kg of sodium pentobarbital whereby the spontaneous breathing was supported. On the one side of the animals, the femoral artery and vein were exposed and a polyethylene cannula was introduced in both vessels each. The substances to be tested were administered through the venous cannula. The mean arterial blood pressure was measured by connecting the arterial cannula with a Statham P 23 Db pressure transducer and electromanometer.

As a first screening dose, 5 mg/kg of the compounds to be tested were intravenously (i.v.) administered. The results are summarized in Table 1.

TABLE 1

Hypotensive effect of the compounds of the general formula (I) in anaesthetized cats after intravenous administration

| Compound of Example | Dose mg/kg i.v. | Mean arterial pressure decrease Hgmm |
|---|---|---|
| 2 | 1.0 | −90 |
| 4 | 5.0 | −70 |
| 5 | 5.0 | −100 |
| 6 | 5.0 | −35 |
| 7 | 5.0 | −35 |
| 8 | 5.0 | −80 |
| 9 | 5.0 | −55 |
| 3 (or 12) | 5.0 | −95 |
| 10 | 5.0 | −60 |
| 21 | 5.0 | −60 |
| 22 | 5.0 | −35 |
| 23 | 5.0 | −65 |
| 27 | 5.0 | −30 |
| 28 | 5.0 | −50 |

Measurement of the antihypertensive effect of conscious, spontaneously (genetically) hypertensive (SH) rats The systolic blood pressure was indirectly measured by the tail-cuff method. The compounds to be tested were introduced orally (p.o.) to the animals. The blood pressure measurements were made by using a 5-channel automatized equipment. The results are summarized in Table 2.

TABLE 2

Antihypertensive effect of compounds of the general formula (I) on conscious SH rats after oral administration

| Compound of Example | Dose mg/kg p.o. | Decrease in the systolic blood pressure % |
|---|---|---|
| 4 | 50 | −33 |
| 5 | 50 | −42 |
| 5 | 10 | −45 |
| 8 | 50 | −18 |
| 3 (or 12) | 25 | −32 |
| 3 (or 12) | 12.5 | −25 |
| 3 (or 12) | 6.25 | −18 |
| 10 | 50 | −25 |

The results summarized in Tables 1 and 2 show that the compounds of the general formula (I) investigated exert a significant blood pressure lowering action after intravenous or oral administration.

Further on, the action of the compounds of the invention on the adrenergic alpha receptors was studied on isolated organs.

(a) Investigation of the action on the pre- and postsynaptic adrenergic alpha receptors on the stimulated mouse vas deferens The method of Hughes et al. [Brit. J. Phamacol. 51, pp. 139–140P (1975)] was used. The preparations suspended in a modified Krebs solution at 31° C. were excited by the field stimulation method [rectangular paired impulses with 1 msec interval, supramaximal potential (70 to 75 V=8 to 9 V/cm) and 100 msec impulse interval, pairs repeated in each 10 sec]. After stimulation, norepinephrine (NE) was dropped into the organ bath and a dose-response curve was taken up. Thus, the effect of both the endogenous norepinephrine liberated by stimulation and the exogenous norepinephrine could be studied before and after adding the substance to be tested. The results are summarized in Table 3.

TABLE 3

Action of the compounds of general formula (I) on pre- and postsynaptic alpha receptors of the stimulated mouse vas deferens

| Compound of Example | Concentration mole | Inhibition of the stimulation % | Inhibition of the exogenous NE % |
|---|---|---|---|
| 5 | $10^{-7}$ | 16.2 | 81.0 |
| 3 (or 12) | $10^{-7}$ | 0 | 65.0 |
| 3 (or 12) | $10^{-8}$ | 0 | 25.0 |
| 2 | $10^{-7}$ | 0 | 100.0 |

(b) Kinetic analysis on rabbit aorta strip preparation: investigation of the postsynaptic alpha$_1$ receptor antagonism Male rabbits with a body-weight of 3 to 3.5 kg were used for these experiments. The aorta spiral was prepared according to Furchgott and Bhadrakon [J. Pharmacol. Exp. Ther. 108, 129 (1953)]. The spiral preparations were suspended at 37° C. in a Krebs solution containing $10^{-4}$ mole of ascorbic acid and bubbled through by carbogen (95% of oxygen and 5% of carbon dioxide) with an equilibration period lasting 40 to 60 minutes. A dose response curve was plotted by using norepinephrine and a dose selected from the steepest interval of the curve was added repeatedly to the bath until obtaining equal responses. Then, the compound to be tested was added and after 5 minutes, the dose series of norepinephrine was repeated. The extent of the inhibition was expressed as percentage. The results are summarized in Table 4.

TABLE 4

Analysis of the postsynaptic alpha$_1$ receptor-blocking effect

| Compound of Example | pA$_2$* | Slope of the curve |
|---|---|---|
| 3 (or 12) | 7.26 | −1.26 |
| Prazosine reference | 9.45 | −0.96 |

*pA$_2$: Negative logarithm of the molar antagonist concentration inhibiting the agonist to 50%.

It is obvious from Tables 3 and 4 that the tested compounds of the invention exert a strong norepinephrine-inhibiting effect on the adrenergic alpha$_1$-receptors.

The calcium-antagonism of the compounds of the invention was studied on an isolated vessel preparation based on the work of M. Fiol de Cuneo et al. [Arch. Int. Pharmacodyn. 263, 28 (1983)].

Male CFY rats with a body-weight of 150 to 200 g were bled by decapitation and the portal vein was immediately prepared starting from the hepatic portal. The vessel was longitudinally incised, bound to a transducer registering the contractions and incubated under a tension of 1 g at 37° C. in a calcium-free Krebs-Ringer bicarbonate solution aerated with carbogen. After an equilibration lasting for 30 minutes, the functioning of the receptor-mediated and the K$^+$-depolarisation-mediated calcium channels, respectively, were investigated.

For studying the adrenergic receptor-mediated channel, $1 \times 10^{-5}$ mole of norepinephrine and, simultaneously, a compound to be tested were added to the organ bath, the calcium-concentration of the bath was gradually increased to 15 millimoles by adding calcium chloride while measuring the contractions developed.

For investigating the potential-mediated calcium channel, the vein placed in the calcium-free Krebs-Ringer solution was washed by adding and then by removing 80 millimoles of potassium chloride while maintaining the isotania until no contraction appeared on repeatedly adding potassium chloride. After adding the compound to be tested, the calcium concentration of the solution was gradually increased while registering the response.

All measurements were carried out at 37° C. while bubbling through carbogen. By taking various concentrations of the compound to be tested, the concentration was determined which resulted in an inhibition of 50% (IC$_{50}$) as compared to the maximum value measured on the vein incubated without the compound to be tested.

The results are summarized in Table 5.

TABLE 5

Calcium-antagonistic effect of the compounds of general formula (I)

| Compound of Example | Inhibition of the calcium channel | |
|---|---|---|
| | Adrenergic receptor-mediated | Potential-mediated |
| | IC$_{50}$ mole | |
| 2 | $4 \times 10^{-6}$ | $1 \times 10^{-5}$ |
| 4 | $1 \times 10^{-7}$ | $2 \times 10^{-7}$ |
| 5 | $2 \times 10^{-5}$ | $5 \times 10^{-5}$ |
| 3 (or 12) | $4 \times 10^{-7}$ | $5 \times 10^{-7}$ |
| Verapamil (reference) | $1 \times 10^{-6}$ | $8 \times 10^{-8}$ |
| Nifedipine (reference) | $2 \times 10^{-6}$ | $1 \times 10^{-8}$ |
| Prazosine (reference) | $9 \times 10^{-9}$ | $5 \times 10^{-4}$ |

It can be seen from Table 5 that the tested compounds of the invention exert a strong inhibition on the adrenergic receptor-mediated as well as on the potential-mediated calcium-channels.

Several of the compounds of the invention exert a strong and pronounced blood pressure lowering action together with a simultaneous decrease in the heart rate. The blood pressure lowering effect is particularly expressed in case of the compounds of Example 2, 4, 5, 8 and 3 (or 12). After administering the compounds of Examples 5, 8, 3 (or 12) and 10, a significant inhibition of the pressor (blood pressure increasing) effect of epinephrine was observed.

From among the compounds of the invention, the substance described in Example 3 (or 12) proved to be the most preferable on the basis of strength of activity, duration of effect as well as the dose-response correlation. Thus, the detailed and harmonized biological and biochemical study of the compounds of the invention are hereinafter illustrated on the compound of Example 3 (or 12).

Study on the compound of Example 3 (or 12)
Hypotensive and heart rate effects on anaesthetized cats after intravenous or intraduodenal administration The cats were anaesthetized by intraperitoneally administering 35 mg/kg of sodium pentobarbital while promoting the spontaneous respiration by the introduction of a trachea cannula. On one side, the femoral vessels are cannulated. The cannula introduced to the femoral vein was used for the intravenous administration of the compounds to be tested. The arterial cannula was connected with a Hellige electromanometer by using a Statham P 23 Db transducer for measuring the mean arterial pressure. The heart rate was continuously registered by means of a cardiotachometer triggered by the pulse wave sign of the electromanometer.

In an other series of these experiments, the compound to be tested was administered through a duodenal tube. The compound of Example 3 (or 12) was used in intravenous doses of 0.5, 1.0 and 5.0 mg/kg as well as in intraduodenal doses of 1.25, 5.0 and 10.0 mg/kg.

The following results were obtained.

A very strong hypotension of 50% was caused by the lowest intravenous dose (0.5 mg/kg) of the compound of Example 3 (or 12) with a half-life of about 30 minutes. This hypotension lasted for 60 minutes and was accompanied by bradycardia.

A strong hypotension was also observed after an intraduodenal administration: a decrease of 50% in the blood pressure was obtained by using the lowest dose of 1.25 mg/kg. This action developed within 15 minutes and could be detected up to 2 hours after administration. The heart rate was significantly diminished. It is important that the maximum of the hypotension was nearly equal after either the intravenous administration of 1.0 mg/kg or the intraduodenal administration of 1.25 mg/kg.

Hypotensive and heart rate effects of anaesthetized dogs after intravenous or intraduodenal administration Beagle dogs of both sexes were anaesthetized by the intravenous administration of 40 mg/kg of sodium pentobarbital. A cannula was introduced to the femoral artery and vein each on one side for the intravenous administration of the compounds to be tested as well as for measuring the blood pressure.

In an other series of these experiments, the substances were administered through a duodenal tube. Similarly to the experiments carried out on cats, the systemic arterial blood pressure was measured by using an electromanometer and the cardiotachometer was triggered by the heart rate wave sign.

The renal artery on one side was exposed retroperitoneally and fitted with an electromagnetic flow-meter head for measuring the blood flow of the renal arterial vascular bed and for determining the local vascular resistance. Prazosine and verapamil were used as reference drugs. The following results were obtained.

A decrease of 50% or 30%, respectively, in the systemic arterial blood pressure was observed after the intravenous or intraduodenal, respectively, administration of 1.0 mg/kg of the compound of Example 3 (or 12). After intravenous administration, the half-life of the effect was 30 minutes. After intraduodenal administration, the maximum effect developed in the 5th minute, remained constant for 30 minutes and was only halved at the end of the first hour. After intravenous administration, bradycardia was observed during the first 5 minutes, then the alteration was not significant. After intraduodenal administration, tachycardia of about 20% developed.

The same hypotensive effect was obtained after the intravenous administration of 0.25 mg/kg of prazosine; however, the hypotensive action of 1 mg/kg of intraduodenally administered prazosine was only the half of that observed after the same intraduodenal dose of the compound of Example 3 (or 12).

Verapamil (used as an other reference drug) caused a decrease of 20% in the systemic arterial blood pressure after an intravenous dose of 0.25 mg/kg. After an intraduodenal dose of 10 mg/kg, the hypotension was only 30% and the maximum effect developed after 30 minutes.

Thus, the compound of Example 3 (or 12) used as an illustrating Example showed a strong hypotensive effect on an anaesthetized normotensive dog after both intravenous and intraduodenal administrations. The activity of this compound reached that of prazosine after intraduodenal administration and was higher than that of verapamil by using any of the two routes of administration.

The resistance of the renal artery was diminished by about 40% after 1 mg/kg intravenous dose of the compound of Example 3 (or 12) while a decrease of about 20% in the resistance was caused by an intravenous dose of 0.25 mg/kg of prazosine. After intraduodenal administration of 1.0 mg/kg, the resistance-diminishing action of prazosine was equal to that obtained after an intraduodenal dose of 1.0 mg/kg of the compound of Example 3 (or 12) (i.e. about 40%).

Verapamil caused a decrease of about 25% in the resistance of the renal artery after both an intravenous dose of 0.25 mg/kg or an intraduodenal dose of 10 mg/kg. Thus, the peripheral vasodilatory action of the compound of Example 3 in the renal vascular bed reached or eventually surpassed the activity of prazosine and produced stronger effects than verapamil.

Investigation of the antihypertensive effect on conscious hypertensive rats after acute and subacute treatments These experiments were accomplished on conscious spontaneously hypertensive (SH) and renally hypertensive rats.

The systolic blood pressure and heart rate of the animals were indirectly measured by using the tail-cuff method by means of a 5- channel automatized equipment. The compound of Example 3 (or 12) and the reference drugs, verapamil and prazosine, were given orally.

The subacute experiments were carried out on SH rats by administering daily twice a 3 mg/kg intraperitoneal dose for 14 days.

The following results were obtained:

An oral dose of 6.25, 12.5 or 25.0 mg/kg of the compound of Example 3 (or 12), or 1.25 mg/kg or 2.5 mg/kg of prazosine, or 50 mg/kg of verapamil were administered to conscious SH rats.

A significant (29%) antihypertensive effect was observed after the lowest dose (6.25 mg/kg) of the compound of Example 3 (or 12) which developed within one hour after treatment while a hypotensive of 16% was observed up to the 5th hour following the treatment. The level and duration of the antihypertensive effect were increased by increasing the doses. After the administration of the highest dose, an antihypertensive effect of 24% was observed in the 8th hour following the treatment.

An 1.25 mg/kg dose of prazosine resulted in an antihypertensive effect of 26% in the 5th hour following treatment.

Verapamil even in a dose of 50 mg/kg did not give a higher antihypertensive effect (30%) than did the compound of Example 3 (or 12) in the above-mentioned much lower doses.

Within this test, no significant heart rate alteration was caused either by the compound of Example 3 (or 12) or any of the reference drugs.

An oral dose of 3.125, 12.5 or 25.0 mg/kg of the compound of Example 3 (or 12), or 1.25 mg/kg of prazosine, or 50 mg/kg of verapamil was administered to conscious renal hypertensive rats.

The maximum antihypertensive effects (16, 24 and 27%, respectively) of the compound of Example 3 (or 12) developed in the 1st to 2nd hours. After the highest dose (25 mg/kg), this effect was significant even in the 8th hour following the treatment.

Similarly to the results obtained on SH rats, prazosine in a dose of 1.25 mg/kg caused a hypotension of 26% which was found to be 20% in the 5th hour following the treatment.

A much higher dose of verapamil (50 mg/kg) resulted only in an antihypertensive effect which was equal to that of the compound of Example 3 (or 12).

Within this test, a moderate tachycardia (18%) was caused by the compound of Example 3 (or 12) which, however, disappeared in the 2nd to 3rd hours after the treatment. The heart rate was not significantly influenced by any of the two reference drugs.

During the subacute treatments, the maximum effect (22%) of the compound of Example 3 (or 12) developed on the 10th day. This value was not altered on the following days of treatment. No signs of tachyphylaxia were observed.

Study on the acute toxicity of the compound of Example 3 (or 12)

Male and female CFY rats and mice were used. The animals were observed for 14 days following the single administration of the compound.

The following results were obtained.

|  | Rats |
|---|---|
| Female: | $LD_{50}$ i.p. = 97.76 (74.91–127.57) mg/kg |
| Male: | $LD_{50}$ i.p. = 116.18 (96.2–140.28) mg/kg |
| Female: | $LD_{50}$ p.o. = 400 mg/kg |
| Male: | $LD_{50}$ p.o. = 600 mg/kg |
|  | Mice |
| Female: | $LD_{50}$ i.p. = 160 mg/kg |
| Male: | $LD_{50}$ i.p. = 160 mg/kg |
| Female: | $LD_{50}$ p.o. = 200 mg/kg |
| Male: | $LD_{50}$ p.o. = 300 mg/kg |

On the basis of the pharmacological and biochemical results, the compounds of the general formula (I) of the invention are endowed or adrenergic alpha-receptor-blocking and calcium-antagonizing properties. Several compounds of the invention, particularly the compound described in Example 3 (or 12), are very effective blood pressure lowering agents. Thus, the compounds of the invention may be utilized for a "combined attack" treatment of hypertension. The valuable effect and low toxicity together provide an advantageous therapeutic safety and, considering the novel type of the compounds, significantly contribute to the enrichment of the drug treasure.

The main therapeutic advantage of the compounds of general formula (I) consists in the fact that the alpha$_1$-receptor-blocking and calcium-antagonizing properties are combined in one and the same molecule whereby the side-effects of opposite direction observed separately with the known alpha$_1$-receptor-blockers and calcium-antagonists are eliminated. Furthermore, the compounds can be used to the treatment of some arrhytmias of ventricle origin.

For therapeutical purposes, the daily dose of the compounds of the invention amounts commonly to 0.05 to 2.0 mg/kg of body-weight, preferably to 0.1 to 0.5 mg/kg of body-weight which is administered daily, optionally divided to several doses with consideration of the absorption conditions, or in a sustained release form.

The invention also relates to pharmaceutical compositions containing the compounds of the general formula (I) or the phramaceutically acceptable acid addition salts thereof as active ingredients as well as to the preparation of these compositions.

For therapeutic use, the active compounds according to the invention are suitably formulated to pharmaceutical compositions by mixing them with the commonly used, non-toxic, inert, solid or liquid pharmaceutical carriers and/or auxiliary materials useful for enteral or parenteral administration. As carriers, e.g. water, gelatine, lactose, starch, pectin, magnesium sterate, steric acid, talc or vegetable oils can be used. As auxiliary materials, e.g. preservatives and wetting as well as emulsifying, dispersing, and aromatizing agents and buffers can be employed.

By using the above-metnioned carriers and auxiliary materials, the active agents of the invention may be transformed to the usual pharmaceutical compositions, e.g. to solid compositions (such as tablets, capsules, pills or supporitories) or liquid compositions (such as aqueous or oily solutions, suspensions, emulsions or syrups) as well as to injectable solutions, suspensions or emulsions.

The invention is illustrated in detail by the aid of the following non-limiting Examples.

EXAMPLE 1

Preparation of
2-(3-chloro-1-propyl)-6-chloro-3(2H)-pyridazinone

Step (A)

Preparation of
3-(6-chloro-3-pyridazinyl)-oxy-1-propanol 10.72 g (0.47 g-atom) of sodium are portionwise added to 472 ml (6.5 moles) of 1,3-propanediol at 20° C. under stirring. To the thus-obtained solution 63.2 g (0.42 mole) of 3,6-dichloropyridazine are added and the reaction mixture is stirred at 100° C. for one hour. Thereupon, the mixture is evaporated to dryness under reduced pressure, the evaporation residue is taken up in 200 ml of water and extracted with 500 ml of chloroform. The organic extract is dried over anhydrous sodium sulfate, then the solvent is removed under reduced pressure. The residue is fractionally distilled to give 51.5 g (64.3% yield) of the aimed compound, b. p. 148°–150° C./66 Pa.

IR (KBr, cm$^{-1}$): $\nu$OH: 3600–3100.

$^1$H-NMR ($\delta$ppm, CDCl$_3$): 2.1 (q, 2H, CH$_2$CH$_2$OH) (J=7 Hz); 3.85 (t, 2H, CH$_2$OH) (J=7 Hz); 4.7 (t, 2H, OCH$_2$) (J=7 Hz), 7.0 [d, 1H, c(4)-H] (J=9 Hz); 7.4 [d, 1H, C(5)-H] (J=9 Hz).

The product of Step (A) can be synthetized also in the following way.

A mixture containing 300 ml (4.14 moles) of 1,3-propanediol, 22.4 g (0.2 mole) of potassium tertiary-butoxide and 25 g (0.17 moles) of 3,6-dichloropyridazine is stirred at room temperature for one hour, then the mixture is evaporated to dryness under reduced pressure. The residue is taken up in 100 ml of water and extracted with 300 ml of chloroform. The organic layer is dried over anhydrous sodium sulfate and after removing the solvent under reduced pressure, the residue is fractionally distilled to give 25.8 g (82% yield) of the aimed compound, b. p. 148°–150° C./66 Pa which is in all respects identical with the product of Step (A).

Step (B)

Preparation of
2-(3-chloro-1-propyl)-6-chloro-3(2H)-pryridazinone

To a solution containing 78 g (0.41 mole) of the product prepared in Step A and 64.2 ml (0.46 mole) of triethylamine in 280 ml of absolute dimethyl formamide, 34.7 ml (0.45 mole) of methanesulfonyl chloride are dropped at 5° to 10° C. under stirring during 30 minutes. The reaction mixture is stirred at room temperature for 2 days, then poured into 500 g of ice and extracted twice with 200 ml of ether each. The etheral phases are combined, dried over anhydrous sodium sulfate and the solvent is evaporated under reduced pressure to give the aimed substance as a crude product in a yield of 69.6 g (91%) which can be used for the following reactions without purification.

IR (KBr, cm$^{-1}$): $\gamma$ C=O1666.

EXAMPLE 2

Preparation of 28
3-(benzo[1,4]dioxan-2-yl-methylamino)-1-propyl]-6-chloro-3(2H)-pyridazinone hydrochloride A mixture containing 83 g (0.4 mole) of 2-(3-chloro-1-propyl)-6-chloro-3(2H)-pyridazinone (prepared as described in Example 1), 48.2 g (0.29 mole) of benzo[1,4-]dioxan-2-yl-methylamine and 42 g of powdered anhydrous potassium carbonate in 340 ml of absolute dimethyl formamide is stirred at 90° to 100° C. for 16 hours. After cooling down, the precipitate is filtered off, washed 3 times with 30 ml of dimethyl formamide each and the combined filtrate is evaporated under reduced pressure. The residue is thoroughly triturated with 50 ml of water; the pH value of the thus-obtained mixture is adjusted to 2 by adding an aqueous 10% hydrochloric acid solution and extracted 3 times with 50 ml of ether each. Then, the aqueous phase is alkalized to pH 10 by adding 20% aqueous sodium hydroxide solution and extracted 5 times with 100 ml of ethyl acetate each. The organic phases are combined, dried over anhydrous sodium sulfate and the solvent is removed under reduced pressure. The residue is dissolved in 50 ml of absolute ethanol, clarified as hot with activated charcoal and after filtration the pH value of the filtrate is adjusted to 3 by adding 25% ethanolic hydrogen chloride solution under cooling with ice and stirring. The mixture is kept at 4° C. overnight, the crystalline precipitate is filtered off, washed 3 times with 20 ml of ice-cool absolute ethanol each and dried to give the aimed hydrochloride salt in a yield of 23.2 g (21%), m. p. 162°–165° C.

IR (KBr, cm$^{-1}$): $\nu$NH+ 3100–2400, $\nu$C=O 1645, $\nu$COC 1265.

$^1$H-NMR ($\delta$ppm, DMSO-d$_6$): 2.2 (m, 2H, CH$_2$CH$_2$CH$_2$), 2.9–3.1 (m, 4H, CCH$_2$NCH$_2$CH$_2$), 4.1 (t, 2H, CH$_2$—C$_6$H$_5$), 4.3 (T, 2H, OCH$_2$), 4.7 (m, 1H, OCH), 6.9 (s, 4H, benzodioxane), 7.0 (dd, 1H, pyridazine C(4)-H), 7.5 (dd, 1H, pyridazine C(5)-H), 7.9 (dd, 1H, pyridazine C(3)-H), 9.7 (s, broad, 1H, NH+).

EXAMPLE 3

Preparation of 2-[3-(benzo[1,4]dioxan-2-yl-methylamino)-1-propyl]-3(2H)-pyridazinone hydrochloride A solution containing 30 g (0.08 mole) of 2-[3-(benzo[1,4]dioxan-2-yl-methylamino)-1-propyl]-6-chloro-3(2H)-pyridazinone hydrochloride (prepared as described in Example 2), 600 ml of absolute ethanol and 6.2 g of powdered sodium hydroxide is hydrogenated in the presence of 3 g of 5% palladium-on-charcoal catalyst under atmospheric pressure and at room temperature. After ceasing of the hydrogen uptake, the catalyst is filtered off, washed 3 times with 20 ml of absolute ethanol each and the filtrate is evaporated under reduced pressure. The residue is boiled with 50 ml of absolute isopropanol for 5 minutes and then filtered. The pH value of the filtrate is adjusted to 4 by adding 25% ethanolic hydrogen chloride solution under stirring and cooling with ice. The mixture is kept at 4° C. overnight, the crystalline precipitate is filtered off, washed with ice-cool absolute ethanol and dried to give 17 g (63% yield) of the aimed product, m. p. 131°–132° C. After recrystallization from ethanol, the hydrochloride melts at 133°–136° C.

The componnets of the general formula (I) listed hereinafter in Table 6 were prepraed by using the method described in Example 2 or 3.

EXAMPLE 12

Preparation of 2-[3-(benzo[1,4]dioxan-2-yl-methylamino)-1-propyl]-3(2H)-pyridazinone hydrochloride

Step (A)

Preparation of 3-[N-(benzo[1,4]dioxan-2-yl-methyl)-amino]-1-propanol

A mixture containing 192 g (0.6 mole) of (benzo[1,4]dioxan-2-ylmethyl)4-toluenesulfonate and 208 g (2.77 moles) of 3-amino-1-propanol is heated at 70° C. while stirring for 2 hours. After cooling, the mixture is dissolved in 1000 ml of chloroform and the solution is washed 5 times with 200 ml of water each for removing the excess of 3-amino-1-propanol. The chloroformic phase is dried over anhydrous sodium sulfate, evaporated to dryness under reduced pressure and the dry evaporation residue is thoroughly triturated with 130 ml of ether. After standing the crystalline precipitate is filtered off, washed with a little amount of ether and dried at room temperature to give 96.5 g (72% yield) of the aimed product, m. p. 52°–53 C.

Step (B)

Preparation of 3-[N-benzyl-N-(benzo[1,4]dioxan-2-yl-methyl)-amino]-1-propanol

A mixture containing 223 g (1 mole) of the product prepared as described in Step A), 139 g (1.1 moles) of benzyl chloride, 15 g (0.1 mole) of sodium iodide, 15 g (0.05 mole) of tetra(n-butyl)-ammonium bromide and 414 g (3 moles) of anhydrous potassium carbonate in 2000 ml of absolute toluene is boiled under reflux while stirring for 3 hours. After cooling down, the solid precipitate is filtered off and washed twice with 200 ml of toluene each. The combined filtrate is washed with 500 ml of water and then twice with 600 ml of 1N aqueous hydrochloric acid solution. The combined acidic extract is alkalized up to pH 9 by adding 1N aqueous sodium hydroxide solution and extracted 3 times with 600 ml of dichloromethane each. The combined organic extract is dried over anhydrous sodium sulfate and evaporated to dryness under reduced pressure to give 256 g (82% yield) of the aimed product.

IR (KBr, cm$^{-1}$): $\nu$OH 3381, $\nu$COC 1265.

$^1$H-NMR ($\delta$ppm, CDCl$_3$): 1.9 (m, 2H, CH$_2$CH$_2$CH$_2$), 2.8 (m, 2H, CCH$_2$NCH$_2$CH$_2$), 3.8 (m, 5H, OCH$_2$, OCH, CH$_2$OH), 4.2 (m, 2H, CH$_2$C$_6$H$_5$), 6.85 (s, 4H, benzodioxane), 7.35 (m, 5H, phenyl).

TABLE 6

Compounds of the general formula (I), wherein R stands for (CH$_2$)$_3$—NR$^1$R$^2$

| Compound of Example | X | NR$^1$R$^2$ | Hydrochloride, m.p. °C. |
|---|---|---|---|
| 4 | Cl | 2-phenoxyethylamino | 113–115 |
| 5 | H | 2-phenoxyethylamino | 138–140 |
| 6 | 1-pyrrolyl | 2-phenoxyethylamino | 143–145 |
| 7 | Cl | 2-(phenylthio)-ethylamino | 106–108 |
| 8 | Cl | 2-(2-chlorophenoxy)-ethylamino | 130–135 |
| 9 | H | 3-phenoxy-1-propylamino | 149–153 |
| 10 | H | 2-(2-fluorophenoxy)-ethylamino | 87–88 |
| 11 | Cl | amino | 245–248 |

Step (C)

Preparation of
3-[N-benzyl-N-(benzo[1,4]dioxan-2-yl-methyl)-amino]-1-propyl chloride hydrochloride 59 ml (0.82 mole) of thionyl chloride are dropped to a solution containing 256 g (0.82 mole) of the product prepared as described in Step (B) in 1000 ml of absolute dichloromethane under stirring. During the reaction, the solution begins to boil. After ending the addition, the reaction mixture is boiled under reflux while stirring for 4 hours and then set aside at 4° C. overnight. Then the crystalline precipitate is filtered off, washed twice with 150 ml of absolute acetone each and dried over phosphorus pentoxide under reduced pressure to give 298 g (99% yield) of the aimed product, m. p. 144°–145° C.

IR (KBr, cm$^{-1}$): $\nu$NH$^+$ 2775, $\nu$COC 1265.

$^1$H-NMR ($\delta$ppm, CDCl$_3$): 2.4 (m, 2H, CH$_2$Ch$_2$CH$_2$), 3.2 (m, 4H, CCH$_2$NCH$_2$CH$_2$), 3.6 (t, 2H, CH$_2$Cl), 3.9–4.3 (m, 4H, OCH$_2$, CH$_2$C$_6$H$_5$), 4.8 (m, 1H, OCH), 6.7–7.1 (m, 5H, phenyl), 6.8 (s, 4H, benzodioxane), 10.0 (s, broad, 1H, NH).

Step (D)

Preparation of
2-{3-[N-benzyl-N-(benzo[1,4]dioxan-2-yl-methyl)-amino]-1-propyl}-3(2H)-pyridazinone A solution containing 80 g (0.217 mole) of the product prepared as described in Step C) in 400 ml of methanolic potassium hydroxide solution (containing 13.6 g of 90% potassium hydroxide) is stirred for 15 minutes and then evaporated to dryness under reduced pressure. The residue is stirred with 1200 ml of absolute toluene and the undissolved potassium chloride is filtered off.

Simultaneously, 31.2 g (0.325 mole) of 3(2H)-pyridazinone is stirred with 400 ml of a methanolic solution containing 20.4 g of 90% of potassium hydroxide for 30 minutes, then the mixture is evaporated to dryness under reduced pressure and twice 50 ml of absolute toluene each are distilled off from the residue to give a dry substance of 44 g which contains the potassium salt of 3(2H)-pyridazinone.

33 g of the latter potassium salt are added to the above-prepared toluene solution containing 3-[N-benzyl-N-(benzo[1,4]dioxan-2-yl-methyl)-amino]-1-propyl chloride base, 12 g (0.037 mole) of tetra(n-butyl)-ammonium bromide are added and the mixture is boiled under reflux while stirring for 4 hours. Then further 11 g of the above potassium salt are added to the reaction mixture, and after adding 3 g of 90% powdered potassium hydroxide and 3 g (0.0093 mole) of tetra(n-butyl)-ammonium bromide, the reaction mixture is boiled under reflux while stirring for further 3 hours. After cooling down, the reaction mixture is extracted twice with 100 ml of 2N sodium hydroxide solution each, then twice with 200 ml of 6% sodium hydrogen carbonate solution and finally 3 times with 400 ml of water. The organic layer is dried over anhydrous sodium sulfate and the solution is evaporated to dryness under reduced pressure to give 75.6 g (89% yield) of the aimed product which is oily but can be used in the following step without purification.

IR (KBr, cm$^{-1}$): $\nu$COC 1265.

$^1$H-NMR ($\delta$ppm, CDCl$_3$): 2.0 (m, 2H, CH$_2$CH$_2$CH$_2$), 2.6 (m, 4H, CCH$_2$NCH$_2$CH$_2$), 3.4–4.4 (m, 7H, OCH$_2$, OCH, CH$_2$C$_6$H$_5$, CH$_2$CH$_2$N), 6.8 (s, 4H, benzodioxane), 7.0–7.3 and 7.3 (m and s, 7H, phenyl and pyridazine C(4)-H, C(5)-H), 7.7 (m, 1H, pyridazine C(3)-H).

Step (E)

Preparation of
2-[3-(benzo[1,4]dioxan-2-yl-methylamino)-1-propyl]-3(2H)-pyridazinone hydrochloride To a solution containing 75.6 g (0.193 mole) of the product of Step (D) in 700 ml of absolute ethanol, 30.2 ml of aqueous concentrated hydrochloric acid, 68 ml of water and 12.0 g of a 10% palladium-on-charcoal catalyst are added, and the mixture is hydrogenated at a temperature of 20° C. and atmospheric pressure. After cessation of the hydrogen absorption, the catalyst is filtered off and the pH value of the ethanolic solution is adjusted to 7 by adding 1N aqueous sodium hydroxide solution. After removing the ethanol at a temperature of 50° C. under reduced pressure, the residue is dissolved in 500 ml of water and the pH value of the solution is adjusted to 2 by adding 2N aqueous hydrochloric acid solution. The aqueous solution is extracted 3 times with 150 ml of dichloromethane each, then th pH value of the aqueous solution is adjusted to 9 and the aqueous phase is extracted 3 times with 200 ml of chloroform each. The combined chloroformic phase is dried over anhydrous sodium sulfate and evaporated to dryness under reduced pressure. The residue is dissolved in 120 ml of absolute ethanol and the pH value of the solution is adjusted to 5 by adding 22% ethanolic hydrogen chloride at 0° C. while stirring.

The mixture is kept in a refrigerator at 4° C. overnight, the crystalline precipitate is filtered off, washed with ice-cold ethanol and dried over phosphorus pentaoxide at 50° C. under reduced pressure to give 40.1 g (61.5% yield) of the aimed product, i.e. the product of Example 12, m.p. 131°–13° C. After recrystallization from ethanol, the melting point raises to 133°–136° C. The thus-obtained hydrochloride is identical to that described in Example 3.

The title product of Example 12 [i.e. the product of Example 12, Step E)] can also be prepared from the product of Example 12, Step (D) in the following way.

1.07 g of a 10% palladium-on-charcoal catalyst and 5 ml of freshly distilled cyclohexene are added to a solution containing 1.95 g (5 mmoles) of the product of Example 12, Step D) in 15 ml of acetic acid and the mixture is boiled under reflux for 2 hours. After cooling down, the catalyst is filtered off, washed twice with 5 ml of water each, then the pH value of the filtrate is adjusted to 9 by adding 50% sodium hydroxide solution and extracted 4 times with 15 ml of chloroform each. The combined organic phase is dried over anhydrous potassium carbonate and evaporated to dryness under reduced pressure to give 1.34 g (80% yield) of the product of Example 12 [i.e. the product of Example 12, Step E)] which may be converted to its hydrochloride (m. p. 130°–132° C.) in the way as described in Example 3. After recrystallization from ethanol, the hydrochloride melts at 133°–136° C.

EXAMPLE 13

Preparation of
2-[2-(2-phenoxyethylamino)-ethyl]-6-(1-imidazolyl)-3(2H)-pyridazinone dihydrochloride

Step (A)

Preparation of 6-(1-imidazolyl)-3(2H)-pyridazinone 9.93 g (0.055 mole) of 6-(1-imidazolyl)-3-chloropyridazine [prepared according to J. Med. Chem. 24, 59 (1981)] are boiled with 7.7 g (0.0781 mole) of fused potassium acetate in 114 ml of acetic acid under reflux for 10 hours and then evaporated to dryness under reduced pressure. The residue is taken up in 200 ml of chloroform, the precipitate is filtered off, washed 4 times with water, then with ether and diisopropyl ether and dried to give 4.9 g (55% yield) of the aimed product, m. p. 239°–240° C.

Step (B)

Preparation of
2-{2-[N-benzyl-N-(2-phenoxyethyl]-aminoethyl}-6-(1-imidazolyl)-pyridazinone dihydrochloride 2.43 g (0.015 mole) of 6-(1-imidazolyl)-3(2H)-pyridazinone are dissolved in the solution of 0.35 g (0.015 g-atom) of sodium in 12 ml of absolute ethanol and the solution is stirred at room temperature for 15 minutes. To the thus-obtained suspension, the base liberated from the solution of 4.89 g (0.015 mole) of N-(2-chloroethyl)-N-(2-phenoxyethyl)-N-benzylamine hydrochloride [dissolved in 12 ml of absolute ethanol by adding a solution of 0.35 g (0.015 g-atom) of sodium in 12 ml of absolute ethanol] is added, thereupon the mixture is stirred at room temperature for 30 minutes and then boiled under reflux while stirring for 4 hours, set aside overnight at room temperature and evaporated. The residue is taken up in 200 ml of chloroform, filtered, the organic solution is washed with water, dried and evaporated under reduced pressure. The residue weighing 5.82 g is dissolved in absolute acetone and a calculated amount of ethanolic hydrogen chloride solution is added, diluted with isopropanol and kept in the refrigerator overnight. The precipitate is filtered off, washed with acetone and dried to give 5.9 g (80% yield) of the aimed product, m. p. 153°–156° C.

IR (KRr, cm$^{-1}$): $\nu$NH+ 2500, $\nu$C=O1672, $\nu$COC 1236, $^1$H-NMR ($\delta$ppm, DMSO-d$_6$): 3.7 (m, 4H, CH$_2$NCH$_2$), 4.5 (m, 4H, NCH$_2$, OCH$_2$), 4.7 (m, 2H, CH$_2$C$_6$H$_5$), 6.7–7.4 (m 12H, phenyl, pyridazine), 8.2 (s, 2H, imidazole C(4)-H, C(5)-H).

N-(2-Chloroethyl)-N-(2-phenoxyethyl)-N-benzyl-amine hydrochloride used as starting material is a known substance [J. Med. Pharm. Chem. 1, 327 (1957); and U.S. Pat. No. 2,688,639].

Step (C)

Preparation of
2-[2-(2-phenoxyethylamino)-ethyl]-6-(1-imidazolyl)-3(2H)-pyridazinone hydrochloride The process described in Example 12, Step (E) is followed, except that the product prepared as described in the preceeding Step (B) is used as starting material to give the aimed product in a yield of 60%, m. p. 200°–203° C.

The following two compounds were prepared analogously to the process described in Example 13:

EXAMPLE 14

2-{3-[N-Benzyl-N-(benzo[1,4]dioxan-2-yl-methyl)-amino]-1-propyl}-6-(4-morpholinyl)-3(2H)-pyridazinone, an oily product; the hydrochloride melts at 193°–196° C.

EXAMPLE 15

2-[3-(Benzo[1,4]dioxan-2-yl-methylamino)-1-propyl]-6-(4-morpholinyl)-3(2H)-pyridazinone dihydrochloride, m. p. 186°–189° C.

The compounds of the general formula (I) listed hereinafter in Table 7 were prepared by using the method described in Example 13.

TABLE 7

Compounds of the general formula (I), wherein R stands for (CH$_2$)$_2$—NR$^1$R$^2$

| Compound of Example | X | NR$^1$R$^2$ | Hydrochloride m.p. °C. |
|---|---|---|---|
| 16 | 3,5-Dimethyl-1-pyrazolyl | [N—Benzyl-N—(2-phenoxyethyl)]-amino | 188–190 |
| 17 | 3,5-Dimethyl-4-nitro-1-pyrazolyl | [N—Benzyl-N—(2-phenoxyethyl)]-amino | 157–160 |
| 18 | H | [N—Benzyl-N—(2-phenoxyethyl)]-amino | 152–154 |
| 19 | 4-Morpholinyl | [N—Benzyl-N—(2-phenoxyethyl)]-amino | 100–103 |
| 20 | H | [N—Benzyl-N—(benzo[1,4]dioxan-2-yl-methyl)]-amino | 164–166 |
| 21 | H | 2-Phenoxyethylamino | 159–161 |
| 22 | 4-Ethoxycarbonyl-1-piperazinyl | 2-Phenoxyethylamino | 147–149 |
| 23 | 3,5-Dimethyl-1-pyrazolyl | 2-Phenoxyethylamino | 98–100 |
| 24 | 4-Ethoxycarbonyl-1-piperazinyl | [N—Benzyl-N—(2-phenoxyethyl)]-amino | 149–151 |
| 25 | 4-Morpholinyl | [N—Benzyl-N—(benzo[1,4]dioxan-2-yl-methyl)]-amino | 165–167 |
| 26 | 4-Ethoxycarbonyl-1-piperazinyl | [N—Benzyl-N—(benzo[1,4]dioxan-2-yl-methyl)]-amino | 162–165 |
| 27 | H | (Benzo[1,4]dioxan-2-yl-methyl)-amino | 163–165 |
| 28 | 4-Morpholinyl | 2-Phenoxyethylamino | 143–145 |

Examples for the preparation of pharmaceutical compositions

EXAMPLE 29

Preparation of tablets

| Composition (for 1000 tablets) | g |
|---|---|
| Hydrochloride of the compound of Example 3 | 10 |
| Lactose | 185 |

-continued

| Composition (for 1000 tablets) | g |
|---|---|
| Microcrystalline cellulose | 25 |
| Talc | 5 |
| Corn starch | 73 |
| Magnesium stearate | 2 |
| Total: | 300 |

The above ingredients are mixed and homogenized, then directly compressed to tablets containing 10 mg of the active ingredient each.

EXAMPLE 30

Preparation of an injectable solution

| Composition (for 2 liters of solution) | |
|---|---|
| Hydrochloride of the compound of Example 3 | 2 g |
| Sodium chloride | 20 g |
| Water for injection purposes q.s. ad | 2000 ml |

We claim:
1. A 3(2H)-pyridazinone of the formula (I)

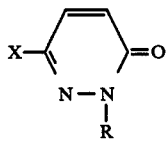

(I)

wherein
R stands for an ethyl or propyl group substituted by a terminal NR$^1$R$^2$ group, wherein
R$^1$ represents a hydrogen atom or a benzyl group,
R$^2$ represents a benzo[1,4]dioxan-2-yl-methyl or -ethyl group or a (CH$_2$)$_n$—R$^3$ group, wherein n is 2 or 3, and
R$^3$ stands for an unsubstituted or a 2-halogen substituted phenoxy group or a phenythio group, and
X stands for a hydrogen or a halogen atom, as well as the pharmaceutically acceptable acid addition salts of these compounds.

2. A compound selected from the group consisting of
2-[3-(benzo[1,4]dioxan-2-yl-methylamino)-1-propyl]-6-chloro-3-(2H)-pyridazinone,
2-[3-(2-phenoxyethylamino)-1-propyl]-6-chloro-3(2H)-pyradazinone,
2-[3-(2-phenoxyethylamino)-1-propyl]-3(2H)-pyridazinone,
2-{3-[2-(2-chlorophenoxy)-ethylamino]-1-propyl}-6-chloro-3(2H)-pyridazinone,
2-[3-(benzo[1,4]dioxan-2-yl-methylamino)-1-propyl]-3(2H)-pyridazinone,
2-{3-[2-(2-fluorophenoxy)-ethylamino]-1-propyl}-3(2H)-pyridazinone
and the hydrochloride of these compounds.

3. A method of treating hypertension comprising administering to a patient a therapuetically effective amount of a 3(2H)-pyridazinone as defined in claim 1.

4. A pharmaceutical composition for treating hypertension in a patient suffering therefrom which comprises:
an effective amount of a compound of the formula I as defined in claim 1 as the active agent and a pharmaceutically acceptable carrier and/or additive.

5. A method of treating hypertension comprising administering to a patient a therapeutically effective amount of a 3(2H)-pyridazinone as defined in claim 2.

6. A pharmaceutical composition for treating hypertension in a patient suffering therefrom which comprises:
an effective amount of a compound of the formula I as defined in claim 2 as the active agent and a pharmaceutically acceptable carrier and/or additive.

7. The 3(2H)-pyridazinone of the formula I as defined in claim 1 which is 2-[3-(benzo[1,4]dioxan-2-yl-methylamino)-1-propyl]-3(2H)-pyridazinone hydrochloride.

8. A method of treating hypertension comprising administering to a patient a therapeutically effective amount of 2-[3-(benzo[1,4]dioxan-2-yl-methylamino)-1-propyl-3-(2H)-pyridazinone hydrochloride.

9. The 3(2H)-pyridazinone of claim 1 wherein R$_3$ is an unsubstituted phenoxy group.

* * * * *